United States Patent
Bagala' Rampazzo et al.

(10) Patent No.: US 7,557,249 B2
(45) Date of Patent: *Jul. 7, 2009

(54) SPIROBIFLUORENE DERIVATIVES, THEIR PREPARATION AND USES THEREOF

(75) Inventors: Liliana Bagala' Rampazzo, Rome (IT); Giulia Fioravanti, Rome (IT); Leonardo Mattiello, Rome (IT)

(73) Assignee: Merck Patent GmbH (DE)

( * ) Notice: Subject to any disclaimer, the term of this patent is extended or adjusted under 35 U.S.C. 154(b) by 548 days.

This patent is subject to a terminal disclaimer.

(21) Appl. No.: 10/523,101

(22) PCT Filed: Jul. 31, 2003

(86) PCT No.: PCT/EP03/08465

§ 371 (c)(1), (2), (4) Date: Feb. 1, 2005

(87) PCT Pub. No.: WO2004/013080

PCT Pub. Date: Feb. 12, 2004

(65) Prior Publication Data

US 2006/0006365 A1    Jan. 12, 2006

(30) Foreign Application Priority Data

Aug. 1, 2002  (IT) .................... RM2002A0411

(51) Int. Cl.
*C07C 49/00* (2006.01)
*H01L 51/54* (2006.01)
(52) U.S. Cl. ..................... 568/326
(58) Field of Classification Search ........... 428/690, 428/917; 252/301.16–301.35; 568/303–332
See application file for complete search history.

(56) References Cited

U.S. PATENT DOCUMENTS 4,898,983 A * 2/1990 Towle ............ 568/322
5,840,217 A  11/1998 Lupo et al.
7,345,301 B2 * 3/2008 Gerhard et al. .......... 257/40

FOREIGN PATENT DOCUMENTS

EP    0 676 461    10/1995

OTHER PUBLICATIONS

Pedersen, et al. "New methods for the accurate determination of extinction and diffusion coefficients of aromatic and heteroaromatic radical anions in N,N-dimethylformamide," Journal of Electroanalytical Chemistry, 454 (1988), pp. 123-143.*

* cited by examiner

*Primary Examiner*—Marie R. Yamnitzky
(74) *Attorney, Agent, or Firm*—Connolly Bove Lodge & Hutz LLP

(57) ABSTRACT

The invention concerns Spirobifluorene derivatives having the general formula (II) and the corresponding, radical anions that can be represented via the general formula (II):

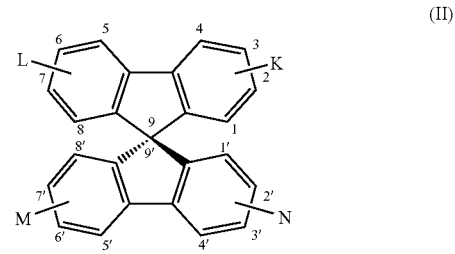

(II)

in which K, L, M and N, the same or different from each other, are independently: H or A-C=O, with the proviso that it is never K=L=M=N=H, wherein A is an aromatic group, possibly substituted with at least an R' group selected in the group of the substituents commonly used in organic chemistry and/or at least one R group where R=aliphatic radical.

The invention also concerns the method for preparing said derivatives and radical anions. Said compounds are applied in the field of components for molecular electronics, in particular systems for electroluminescence, molecular-based computational systems, OLEDs, molecular switching components, components for non-linear optics, field-effect transistors and semiconductors with negative differential resistance.

5 Claims, No Drawings

SPIROBIFLUORENE DERIVATIVES, THEIR PREPARATION AND USES THEREOF

RELATED APPLICATIONS

This application is a national stage application (under 35 U.S.C. 371) of PCT/EP03/008465, filed on Jul. 31, 2003 which claims benefit to Italian application no. RM2002A000411 filed Aug. 1, 2002.

1. Field of the Invention

The present invention concerns derivatives of Spirobifluorene, hereinafter also called SBF, having general formula (II), the method for preparing said compounds and uses thereof, in particular their use in the field of molecular electronics.

2. Prior Art

Spirobifluorenes are a class of spiro-compounds well-known in organic chemistry [(9,9'-Spirobi[9H-fluorene])] and are generally characterised by the following formula (I):

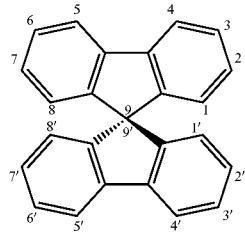
(I)

Their preparation is described by Haas G. and Prelog V., Helv. Chim. Acta (1969) 52, pp. 1202-1218 and their applications are described in Aviram A., J. Am. Chem. Soc. (1988) 110, pp. 5687-92.

The SBFs are a class of organic molecules that can be used instead of their corresponding inorganic species in the arrangement and production of electronic circuits and switches.

The U.S. Pat. No. 5,840,217 describes derivatives of SBF for use as materials for electroluminescence.

The inventors have now found a class of compounds, derivatives of SBF, with particularly interesting chemical-physical characteristics for use in the field of molecular electronics. The general term molecular electronics refers to the technical field in which organic molecular species can be used for electronic applications Molecular Electronics: science and technology" Aviram A. and Ratner M. editors, Annals of the New York Academy of Science, Vol. 1852 (1998), comprising the techniques of electroluminescence and photoluminescence.

SUMMARY OF THE INVENTION

Objects of the present invention are derivatives of SBF, in particular the benzoyl derivatives having the following general formula (II):

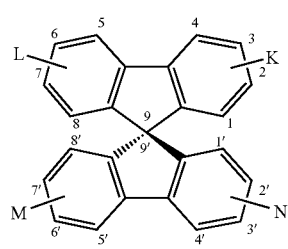
(II)

in which K, L, M and N, the same or different from each other, are independently:
H or

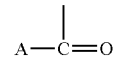

(in the following indicated as A-C=O), with the proviso that it is never K=L=M=N=H, wherein A is an aromatic group, possibly substituted with at least an R' group selected in the group of the substituents commonly used in organic chemistry and/or at least one R group where R=aliphatic radical.

Another object of the invention are the enantiomers corresponding to the compounds of formula (II).

Another object of the invention are the radical anions corresponding to the compounds of formula (II). Radical anion is the chemical species obtained by the addition of an electron to the corresponding neutral species.

A further object of the invention is the method for preparing the compounds of formula (II) and the method for preparing the corresponding radical anions.

Yet another object of the invention are the electronic devices, in particular the molecular-based computational systems, the OLEDs (Organic Light Emitting Diodes) and the components for non-linear optics that use the compounds of formula (II) or the corresponding radical anions.

A further object of the invention is the use of the derivatives of SBF and the corresponding radical anions in components for molecular electronics, in particular for the molecular-based computational systems, for the OLEDs and for non-linear optics.

Further objects will become evident from the detailed description of the invention.

DETAILED DESCRIPTION OF THE INVENTION

The present invention refers to the derivatives of SBF of formula (II), i.e. spiro compounds in which at least one substituent is A-C=O, A indicating an aromatic group or a substituted aromatic group, possibly condensed, possibly containing heteroatoms, possibly bearing at least one radical R, with R=H or aliphatic group. Preferably A is an aromatic radical substituted by at least one member selected from the group of halogens, alkyl radical, preferably $C_{1-6}$(alkyl), trifluoromethyl, hydroxyl, —SH, —SC($C_{1-6}$ alkyl), alkoxy, nitro, cyano, —COOH, —COOC($C_{1-4}$ alkyl), —NH$_2$, —NC($C_{1-4}$ alkyl)$_2$, benzyl, benzoyl.

Preferably the A group bears one or more R and/or R' substituents, wherein R is selected in the group of: linear, branched and cyclic aliphatic $C_{1-n}$, with n positive integer ≧0, preferably $C_{1-18}$(alkyl), more preferably $C_{1-6}$(alkyl); and R' is selected in the group of: halogens, trifluoromethyl, hydroxyl, —SH, —SC[$C_{1-6}$(alkyl)], alkoxy, nitro, cyano, —COOH, —COOC[$C_{1-4}$(alkyl)], —NH$_2$, —NC[$C_{1-4}$(alkyl)]C$_2$, benzyl, benzoyl.

According to a preferred embodiment A can be selected in the group of the following derivatives: phenyl, biphenyl, 1-naphthyl, 2-naphthyl, 2-thienyl, 2-furyl, 2-pyrrolyl, 3-thienyl, 3-furyl, 3-pyrrolyl, 9-anthryl, biphenylenyl, perylenyl, fullerenyl, and corresponding derivatives, said derivatives being preferably substituted by at least one R group and/or an R' group, wherein R and R' have the meaning above indicated.

Within the scope of the present invention, and with reference to formula (II), the following compounds are particularly preferred:

the compounds of formula (III):

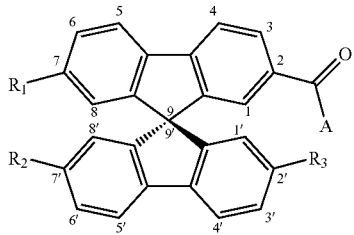

(III)

wherein A has the meaning in the above and $R_1=R_2=R_3=H$; or $R_1=R_3=H$ and $R_2=C_{1-6}$(alkyl); or $R_1=R_2=H$ and $R_3=C_{1-6}$(alkyl); or $R_2=H$ and $R_1=R_3=C_{1-6}$(alkyl);

the compounds of formula (IV):

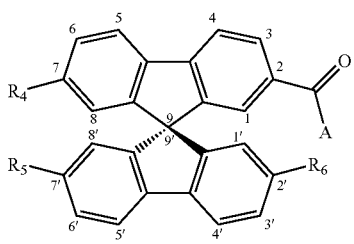

(IV)

wherein $R_5=A-C=O$ with A is as in the above and $R_4=R_6=H$; or $R_5=A-C=O$ and $R_4=R_6=C_{1-4}$(alkyl); or $R_6=A-C=O$ and $R_4=R_5=H$; or $R_6=A-C=O$ and $R_4=R_5=C_{1-4}$(alkyl);

the compounds of formula (V):

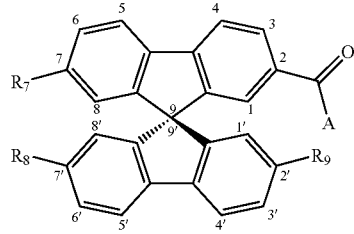

(V)

wherein $R_7=R_9=A-C=O$ and A is as in the above and $R_8=H$; or $R_7=R_9=A-C=O$ and $R_8=C_{1-4}$(alkyl);

the compounds of formula (VI):

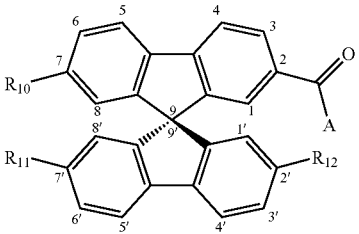

(VI)

wherein $R_{10}=R_{11}=R_{12}=A-C=O$ with A as in the above.

the compounds (VII) wherein L=M=N=H and K=A-C=O in position 2, with A=phenyl and R=H;

the compounds (VIIIa) wherein L=N=H, K and M in position 2 and 2' are A-C=O, with A=phenyl and R=H;

the compounds (VIIIb) wherein L=M=H, K and N in position 2 and 7' are A-C=O, with A=phenyl and R=H;

the compounds (IX) wherein L=M=N=H, K in position 2 is A-C=O, with A=phenyl and R=p-tert-Bu;

the compounds (Xa) wherein L=N=H, K and M in position 2 and 2' are A-C=O, with A=phenyl and R=p-tert-Bu;

the compounds (Xb) wherein is: L=M=H, K and N in position 2 and 7' are A-C=O, with A=phenyl and R=p-tert-Bu;

As some of the molecules of the invention have an axial asymmetry, the corresponding enantiomers fall within the scope of the invention, either in mixtures or as pure compounds.

The presence of the aliphatic R group on the A group, for example the tert-Bu group as in the molecules (IX) and (Xa and Xb), has the advantage of improving solubility in the common solvents, e.g. acetonitrile, dimethylformamide, $CDCl_3$ and other solvents, therefore improving processability and identification by means of the usual spectroscopic analytical techniques.

The COCl intermediates needed for the preparation of the compounds of formula (II) are in most cases commercially available compounds or known compounds, either directly or in the form of the corresponding COOH derivatives. It is common practice to obtain the COCl derivative starting from the corresponding COOH derivative. With particular regard to the fullerenyl derivative, it can be prepared starting from the fullerene compound C60H, ([5,6]Fulleren-C60-lh-1(2H)-yl), Registry Number: 143631-66-7.

The derivatives of the compounds of formula (II) can be prepared according to the standards techniques commonly used in organic chemistry.

A method for preparing the compounds of the invention is based on the use as starting product of the non-functionalised SBF (formula (I)). The method involves the following stages: addition, by means of standard methods (e.g. described in Gore P. H., Chem. Rev. (1955), 55, pp. 229-271)), of A-C=OCl, with A having the above-mentioned meaning, to the non-functionalised SBF (formula (I)). Optimal conditions for obtaining the required compounds are within the capabilities of any technician in the field. A general preparation is given in the following in the experimental part.

An alternative method for preparing the compounds of the invention is based on the use, as intermediate, of SBF functionalised as acid chloride $SBF(COCl)_x$, with x positive integer $\geq 1$ and equal to the number of substituents to be obtained on the SBF. The acid chloride is then combined with A-H, in which A has the above-mentioned meaning. The intermediate acid chloride can be prepared from the corresponding carboxylic acids of the SBF, $SBF(COOH)_x$, in turn obtained from the corresponding acetyl derivatives $SBF(COCH_3)_x$, x having in both cases the above-mentioned meaning.

The compound 9,9'-Spirobi[9H-fluorene]-2,2'-dicarbonyl dichloride ($SBF(COCl)_2$) is known by Registry Number 67665-11-6.

The compounds 9,9'-Spirobi[9H-fluorene]-2-carbonyl chloride, 9,9'-Spirobi[9H-fluorene]-2,2',7-tricarbonyl trichloride and 9,9'-Spirobi[9H-fluorene]-2,2',7-7'tetracarbonyl tetrachloride are new; they can be prepared like the dichloride mentioned above, the preparation of which is illustrated in the examples.

The radical anions of the compounds (II) are obtained preferably via chemical and electrochemical route by the addition of an electron to the corresponding neutral compound; the electrochemical method is particularly preferred as it is easy to perform.

The radical anions of the compounds (VII), (VIIIa, VIIIb), (IX) and (Xa, Xb) are particularly preferred. The electrochemical method for obtaining the radical anions in general is described in "Organic Electrochemistry". Lund H. and Hammerich O. Eds., Marcel Dekker Inc. NY, $4^a$ Ed., (2001).

This method is performed using an electrochemical cell comprising two compartments: one anodic and one cathodic; the cathodic compartment contains a working electrode and a calomel reference electrode. An aprotic solvent is made anhydrous by means of usual procedures (5); a supporting electrolyte is added to it, also made anhydrous, in order to obtain a concentration between 1 M and 0.01 M, preferably 0.2 M and 0.05 M, particularly preferably approximately 0.1 M. A general preparation is given in the following in the experimental part.

The electrolytic solution prepared as described is placed in the anodic compartment that is separated from the cathodic compartment by a portion of the same electrolytic solution appropriately gelled and containing the anode (Pt network). The compound in question is added, under nitrogen, to the cathodic compartment, containing another portion of the same electrolytic solution, in order to obtain concentrations between 0.1 M and 0.1 mM, preferably in the range between 0.01 M and 0.5 mM, particularly preferably approximately 1 mM. An appropriate d.d.p. is applied between the electrodes in order to obtain the required radical anion.

The materials that can be used to build the working electrode are preferably platinum, mercury, lead, silver, composite materials based on Ti, conducting carbon materials, conducting materials containing carbon, vitreous carbon, chemically modified electrodes; vitreous carbon is particularly preferred due to the following characteristics: large applicable d.d.p. window, economic, non-toxic and easy to use. The solvents that can be used are preferably aprotic solvents and their mixtures, for example: acetonitrile, dimethylformamide, N-methylpyrrolidone, dimethylsulfoxide; dimethylformamide is particularly preferred.

The supporting electrolytes that can be used are those preferably containing: perchlorate anions, tetrafluoborate anions, hexafluophosphate anions, lithium cations, sodium cations, tetraalkylammonium cations and related mixtures; the perchlorate anions and tetraethylammonium cations are particularly preferred.

The working temperatures can be between −20° C. and +50° C.; room temperature is particularly preferred.

Due to the presence of the C=O group between the SBF and the A group, the compounds of the invention form the radical anions more easily than corresponding compounds in which the C=O is absent.

In fact it has been observed that the insertion of the C=O functional group results in a considerable improvement of the property of the molecule as it increases its "electron-acceptor" characteristics, shifting the standard potential, E°, of the molecule towards more positive (lower) values. It is known that the standard potential, E°, defined in "Electrochemical methods", Bard A. J. and Faulkner L. R., Wiley, New York. II ed. (2001). p. 3, shifts towards more positive values with respect to a reference molecule when its properties as electron-acceptor are improved with respect to the reference molecule.

With reference to the derivatives of Spirobifluorene with general formula (II) according to the present invention and the corresponding radical anions, the standard potential E° shifts towards more positive values of the quantity $\Delta E°$.

The advantage of the increase of $\Delta E°$ towards more positive potentials with respect to the values of corresponding compounds not containing the functional group C=O is the following: uses of the molecules of the invention involve energy saving with respect to the former. The $\Delta E°$ measured by means of cyclic voltammetry (5) for addition of the substituent R—Ar—C=O according to the invention, with respect to the molecule of the SBF (formula (I)), can be quantified roughly as follows: $\Delta E°$ min 700 mV, for example 860 mV for the compound (mixture of Xa and Xb).

The compounds of the invention and the corresponding radical anions can be advantageously used in the field of electroluminescence in general, in particular light emitting diodes (OLEDs); as components of molecular switching, for non-linear optics; in molecular-based computational systems (the latter described in Aviram A., J. Am. Chem. Soc. (1988) 110, pp. 5687-92); in field-effect transistors (FET) (7)transistors (FET) Laguindanum J. G., Katz H. E., Dodabalapur A. and Lovinger A. J., J. Am. Chem. Soc., (1996) 118. pp. 11331-11332 and in semiconductors with negative differential resistance (NDR).

The compounds according to the invention can be applied in the form of thin films or coating on a suitable substrate according to techniques known to experts in the field. The devices have at least one active layer comprising the compounds of the invention, applied on said substrate.

The following examples are provided to illustrate the invention and should not be considered as restrictive of the scope thereof.

EXAMPLES

Reagents and instruments: carbon sulphide ($CS_2$), dichloromethane ($CH_2Cl_2$) Carlo Erba; aluminium trichloride ($AlCl_3$ Fluka); benzoyl chloride (PhCOCl) Aldrich; tert-Bubenzoyl chloride Aldrich; acetyl chloride (MeCOCl) Fluka; thionyl chloride ($SOCl_2$) Merck; tert-butyl benzene (t-BuBz) Lancaster; IR: Perkin-Elmer 298, Shimadzu 470; NMR: Bruker AC 200.

All carbonyl compounds (4-(nitro)benzoyl chloride, 2-furoyl carbonyl chloride, 4-(fluoro)benzoyl chloride, 4-(methoxy)benzoyl chloride, pentafluorobenzoyl chloride, 2-thienyl carbonyl chloride) were from Lancaster Synthesis Ltd.

Example 1

General Preparation of Mono Derivatives

Acid chloride (1.90 mmol) is dissolved in 20 ml of dichloromethane, cooling to 15° C. under stirring, then added with 274 mg of anhydrous $AlCl_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CHCl_3$, to obtain the mono substituted derivative (yields from 30 to 80%).

Example 2

General Preparation of di-derivatives

Acid chloride (3.48 mmol) is dissolved in 20 ml of dichloromethane, cooling to 15° C. under stirring, then added with 695 mg of anhydrous $AlCl_3$ (5.21 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CHCl_3$, to obtain the di substituted derivative (yields from 70 to 90%).

Example 3

Preparation of the monobenzoyl derivative SBFCOPh (VII)

0.9 g of benzoyl chloride (6.32 mmol) are dissolved in 20 ml of dichloromethane, cooling to 15° C., under stirring, then adding 2.95 g of finely powdered anhydrous $AlCl_3$ (22.12 mmol). 1.0 g of 9,9'-spirobifluorene (I) (3.16 mmol) dissolved in 10 ml of dichloromethane are then added drop wise under stirring for 10 min. The reaction mixture is brought to room temperature and the mixture is then refluxed for one hour. 50 g of ice and 25 ml of a 2N solution of HCl are added to the residue. The water phase is extracted with $CH_2Cl_2$ (3×15 ml).

The combined organic phases are washed with water (20 ml), dried and concentrated until 1.8 g of solid residue are obtained. The product is purified by means of silica gel chromatography with eluant hexane:$CH_2Cl_2$ 70:30 until 1.2 g (90%) of 2-benzoyl-9,9'-spirobifluorene (VII) are obtained; melting point 260-261° C.

2-benzoyl-9,9'-spirobifluorene (VII) (C32 H20 O):

1H-NMR ($CDCl_3$, 200 MHz, δ vs $SiMe_4$): 8.15-6.75 (20 H, mc, ArH).

13C-NMR ($CDCl_3$, 50 MHz, δ vs $SiMe_4$): 196.05 (C═O); 149.11, 148.39, 146.17 140.54, 137.91, 136.91, (all quaternary carbons); 132.13, 131.14, 130.17, 129.84, 129.22, 128.46, 128.27, 128.25, 128.13, 125.56, 124.19, 121.12, 119.64 (all CH); 65.89 (C-spiro); ESI-MS (negative mode): 457.4 (M+H$^+$+2H$_2$O);

IR ($CCl_4$, cm$^{-1}$): 1696 (C═O).

Example 4

Preparation of 2-(p-nitro)-benzoyl-9,9'-spirobifluorene 352 mg of 4-(nitro)benzoyl chloride (1.90 mmol) are dissolved in 20 ml of dichloromethane, cooling to 15° C. under stirring, then added with 274 mg of anhydrous $AlCl_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 310 mg of 2-(p-nitro)-benzoyl-9,9'-spirobifluorene (C32H19NO3; MW=465.51; yields of 42%).

1H-NMR ($CDCl_3$, 200 MHz, δ vs $SiMe_4$): 6.75-8.20 (19 H, mc, ArH).

13C-NMR ($CDCl_3$, 50 MHz, δ vs $SiMe_4$): 194.00 (C═O), 150.14, 149.64, 149.59, 147.52, 147.06, 143.21, 141.86, 140.05, 135.44 (all quaternary carbons), 130.79, 130.67, 130.42, 129.52, 128.10, 127.92, 125.69, 124.34, 123.80, 123.33, 121.07, 120.27, 119.82 (all CH), 65.91 (C-spiro).

IR ($CCl_4$, cm$^{-1}$): 1664 (C═O).

Example 5

Preparation of 2-furoyl-9,9'-spirobifluorene 454 mg of 2-furoyl carbonyl chloride (1.90 mmol) are dissolved in 20 ml of dichloromethane, cooling to 15° C. under stirring, then added with 274 mg of anhydrous $AlCl_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 200 mg of 2-furoyl-9,9'-spirobifluorene (C30H18O2; MW=528.57; yields of 31%).

1H-NMR ($CDCl_3$, 200 MHz, δ vs $SiMe_4$): 6.44-8.08 (18 H, mc, ArH).

13C-NMR ($CDCl_3$, 50 MHz, δ vs $SiMe_4$): 181.68 (C═O), 152.29, 149.70, 149.02, 148.25, 146.78, 146.23, 140.50, 136.67 (all quaternary carbons), 129.98, 129.23, 128.28, 125.02, 124.16, 121.10, 120.18, 119.88, 112.04 (all CH), 65.92 (C-spiro).

IR ($CCl_4$, cm$^{-1}$): 1650 (C═O).

Example 6

Preparation of 2-(p-fluoro)-benzoyl-9,9'-spirobifluorene 301 mg of 4-(fluoro)benzoyl chloride (1.90 mmol) are dissolved in 20 ml of dichloromethane, cooling to 15° C. under stirring, then added with 274 mg of anhydrous $AlCl_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 460 mg of 2-(p-fluoro)-benzoyl-9,9'-spirobifluorene (C32H19FO; MW=438.51; yields 83%).

1H-NMR (CDCl$_3$, 200 MHz, δ vs SiMe$_4$): 6.60-8.00 (19 H, mc, ArH).

13C-NMR (CDCl$_3$, 50 MHz, δ vs SiMe$_4$): 194.56 (C=O), 167.69 (C—F), 162.65 (C—F), 150.01, 149.20, 147.79, 146.09, 141.87, 140.39, 136.71 (all quaternary carbons of SBF), 134.03 (C—C=O of Ph), 132.49, 132.31, 130.46, 129.16 (all CH of SBF), 127.99, 127.89 (CH of Ph, β □□=□), 125.69, 124.30, 123.88, 120.88, 120.21, 119.58 (all CH of SBF), 115.45, 115.02 (CH of Ph, γ □□=□), 65.95 (C-spiro).

IR (CCl$_4$, cm$^{-1}$): 1658 (C=O).

Example 7

Preparation of 2-(p-methoxy)-benzoyl-9,9'-spirobifluorene 323 mg of 4-(methoxy)benzoyl chloride (1.90 mmol) are dissolved in 20 ml of dichloromethane, cooling to 15° C. under stirring, then added with 274 mg of anhydrous AlCl$_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed to reach room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 570 mg of 2-(p-methoxy)-benzoyl-9,9'-spirobifluorene (C33H22O2; MW=450.54; yields of 80%).

1H-NMR (CDCl$_3$, 200 MHz, δ vs SiMe$_4$): 6.84-7.86 (19 H, mc, ArH), 3.78 (3H, s, OCH$_3$).

13C-NMR (CDCl$_3$, 50 MHz, δ vs SiMe$_4$): 194.75 (C=O), 162.90 (C—OMe), 149.851, 148.89, 147.84, 145.45, 141.77, 140.48, 137.44 (all quaternary carbons), 132.22, 130.28, 130.21, 128.87, 127.85, 127.80, 125.51, 124.15, 123.83, 120.72, 120.09, 119.41, 113.33 (all CH), 65.89 (C-spiro), 55.28 (C—OCH$_3$).

IR (CCl$_4$, cm$^{-1}$): 1653 (C=O).

Example 8

Preparation of 2-(pentafluoro)-benzoyl-9,9'-spirobifluorene 473 mg of pentafluorobenzoyl chloride (1.90 mmol) are dissolved in 20 ml of dichloromethane, cooling to 15° C. under stirring, then added with 274 mg of anhydrous AlCl$_3$ (2.05 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 482 mg of 2-(pentafluoro)-benzoyl-9,9'-spirobifluorene (C32H15F5O; MW=510.46; yields of 60%).

1H-NMR (CDCl$_3$, 200 MHz, δ vs SiMe$_4$): 6.80-8.00 (15 H, mc, ArH).

13C-NMR (CDCl$_3$, 50 MHz, δ vs SiMe$_4$): 184.33 (C=O), 150.61, 149.98, 148.71, 147.32, 141.92, 140.03, 139.75, 135.35 (all quaternary carbons), 130.91, 129.91, 129.06, 128.16, 128.03, 124.95, 124.57, 124.39, 123.93, 121.34, 120.63, 120.26, 120.15 (all CH), 65.90 (C-spiro).

IR (CCl$_4$, cm$^{-1}$): 1677 (C=O).

Example 9

Preparation of the di-benzoyl derivative SBF(COPh)$_2$ (mixture of VIIIa and VIIIb)

20 ml of dichloromethane and 0.98 g of benzoyl chloride (6.95 mmol) are placed in a 250 ml Pyrex vessel under stirring. The mixture is cooled to 15° C., then 0.93 g of finely powdered anhydrous AlCl$_3$ (6.95 mmol) are added. Subsequently 1.0 g of 9,9'-spirobifluorene (I) (3.16 mmol) dissolved in 20 ml of dichloromethane are added drop wise under stirring during 30 minutes. The reaction mixture is heated to room temperature and then refluxed for 2 hours. 50 ml of water and ice followed by 20 ml of a 2N solution of HCl are added to the residue. The water phase is extracted with $CH_2Cl_2$ (3×20 ml). The combined organic phases are treated with 20 ml of a saturated solution of $Na_2CO_3$, washed with water (20 ml), dried and concentrated until obtaining 2.1 g of solid residue. The products are purified by means of silica gel chromatography with eluant hexane:$CH_2Cl_2$ 60:40 to give two fractions. In the first fraction, 0.86 g (52%) of 2,2'-dibenzoyl-9,9'-spirobifluorene (mixture of VIIIa and VIIIb) are obtained as a vitreous liquid which eventually solidifies into a waxy solid, and in the second fraction 0.46 g (35%) of 2-benzoyl-9,9'-spirobifluorene (VII), melting point 260-261° C., are obtained.

2,2'-dibenzoyl-9,9'-spirobifluorene (mixture of VIIIa and VIIIb) (C39H24O2):

1H-NMR (CDCl$_3$, 200 MHz, δ vs SiMe$_4$): 8.00-6.75 (24 H, mc, ArH).

13C-NMR (CDCl$_3$, 50 MHz, δ vs SiMe$_4$): 195.80 (C=O), 149.82, 149.02, 147.69, 145.89, 141.72, 140.27, 137.68, 136.60 (all quaternary carbons); 131.94, 130.68, 130.33, 130.38, 129.80, 129.68, 128.99, 128.81, 128.71, 128.14, 128.02, 127.95, 127.77, 127.11, 126.78, 125.58, 124.13, 123.76, 120.78, 120.07, 119.38 (all CH), 65.82 (C-spiro): ESI-MS: (positive mode): 526.6 (M+2H$^+$)

IR: (CCl$_4$, cm$^{-1}$): 1657 (C=O).

Example 10

Preparation of 2,2'-di-(pentafluoro)-benzoyl-9,9'-spirobifluorene 870 mg of pentafluorobenzoyl chloride (3.48 mmol) are dissolved in 20 ml of dichloromethane, cooling to 15° C. under stirring, then added with 695 mg of anhydrous $AlCl_3$ (5.21 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CH_2Cl_2$ 70:30, to obtain 760 mg of 2,2'-di-(pentafluoro)-benzoyl-9,9'-spirobifluorene (C39H14F10O2; MW=704.53; yields of 69%).

1H-NMR ($CDCl_3$, 200 MHz, δ vs $SiMe_4$): 6.80-8.00 (14 H, mc, ArH)

13C-NMR ($CDCl_3$, 50 MHz, δ vs $SiMe_4$): 184.31 (C=O), 149.01, 148.70, 148.57, 139.86, 135.44 (all quaternary carbons), 131.43, 130.11, 128.60, 124.64, 124.26, 121.63, 120.45 (all CH), 65.68 (C-spiro).

IR ($CCl_4$, $cm^{-1}$): 1674 (C=O).

Example 11

Preparation of 2,2'-di-(2-thienoyl)-9,9'-spirobifluorene 510 mg of thiophene 2-carbonyl chloride (3.48 mmol) are dissolved in 20 ml of dichloromethane, cooling to 15° C. under stirring, then added with 695 mg of anhydrous $AlCl_3$ (5.21 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CHCl_3$ 80:20, to obtain 800 mg of 2,2'-di-(2-thienoyl)-9,9'-spirobifluorene (C35H20S2O2; MW=536.67; yields of 94%).

1H-NMR ($CDCl_3$, 200 MHz, δ vs $SiMe_4$): 7.93 (4 H, s); 7.89 (2H, s); 7.58 (2H, s); 7.42 (4H, mc); 7.27 (2H, d); 7.15 (2H, d); 7.01 (2H, t); 6.75 (2 H, d).

13C-NMR ($CDCl_3$, 50 MHz, δ vs $SiMe_4$): 187.31 (C=O), 148.89, 148.25, 145.91, 143.59, 140.49, 137.45 (all quaternary carbons), 134.35, 133.83, 129.81, 129.17, 128.27, 127.77, 124.90, 124.15, 121.04, 119.90 (all CH), 65.89 (C-spiro).

IR ($CCl_4$, $cm^{-1}$): 1680 (C=O).

Example 12

Preparation of 2,2'-di-(p-fluoro-benzoyl)-9,9'-spirobifluorene 551 mg of 4-(fluoro)benzoyl chloride (3.48 mmol) are dissolved in 20 ml of dichloromethane, cooling to 15° C. under stirring, then added with 695 mg of anhydrous $AlCl_3$ (5.21 mmol) finely powdered.

Afterwards 0.5 g of 9,9'-spirobifluorene (1.58 mmol) dissolved in 10 ml of dichloromethane are added drop wise under stirring in a period of 10 minutes.

The reaction mixture is allowed reaching room temperature (RT) then heated, refluxing for 1 hour.

The solvent is evaporated off under vacuum and the residue is added with 50 g of ice and 25 ml of a solution 2N of HCl.

The aqueous phase is extracted with $CH_2Cl_2$ (3×15 ml).

The combined organic phases are washed with a saturated solution of $NaHCO_3$ (20 ml), water (20 ml), dried and concentrated to obtain a solid residue.

The product is purified by silica chromatography with eluant hexane:$CHCl_3$ 80:20, to obtain 700 mg of 2,2'-di-(p-fluoro-benzoyl)-9,9'-spirobifluorene (C39H22F2O2; MW=560.61; yields of 79%).

1H-NMR ($CDCl_3$, 200 MHz, δ vs $SiMe_4$): 6.60-7.90 (22 H, mc, ArH).

13C-NMR ($CDCl_3$, 50 MHz, δ vs $SiMe_4$): 194.45 (C=O), 167.71 (C—F), 162.67 (C—F), 149.02, 148.40, 146.19, 140.47, 136.84 (all quaternary carbons of SBF), 134.06, 134.00, 132.50, 132.32 (all CH of Ph,), 130.87, 129.30, 128.35, 125.45, 124.17, 121.18, 119.74 (all CH of SBF), 115.50, 115.07 (all CH of Ph,), 65.91 (C-spiro).

IR ($CCl_4$, $cm^{-1}$): 1659 (C=O).

Example 13

Preparation of the tert-butyl-benzoyl derivatives: 2-SBF-(CO-p-tert-BuPh) (IX) and 2,2'-SBF-(CO-p-tert-BuPh)$_2$ (Mixture of Xa and Xb)

20 ml of dichloromethane and 1.37 g of 4-tert-butyl-benzoyl chloride (6.95 mmol) are placed in a 250 ml Pyrex vessel under stirring. The mixture is cooled to 15° C., then 0.93 g of very finely powdered anhydrous $AlCl_3$ (6.95 mmol) are added. Subsequently 1.0 g of 9,9'-spirobifluorene (I) (3.16 mmol) dissolved in 10 ml of dichloromethane are added drop wise under stirring for 30 minutes.

The reaction mixture is brought to room temperature and is then refluxed for two hours.

50 ml of water and ice followed by 20 ml of a 2N solution of HCl are added to the residue. The water phase is extracted with $CH_2Cl_2$ (3×20 ml). The combined organic phases are treated with 20 ml of a saturated solution of $Na_2CO_3$, washed with water (20 ml), dried and concentrated until obtaining 2.7 g of solid residue. The products are purified by means of silica gel chromatography with eluant hexane:$CH_2Cl_2$ 60:40 to give two fractions. In the first fraction 0.39 g (26.2%) of 2-(4-tert-butyl-benzoyl) 9,9'-spirobifluorene (IX), m.p. 189-191° C., are obtained and in the second fraction 1.15 g (56.8%) of di-(4-tert-butyl)-benzoyl-9,9'-spirobifluorene (mixture of VIIIa and VIIIb), m.p. 100-105° C. (deliq) are obtained.

2-(4-tert-butyl)-benzoyl-9,9'-spirobifluorene (IX) (C36H28O):

1H-NMR ($CDCl_3$, 200 MHz, δ vs $SiMe_4$): 8.0-6.7 (19H, m, ArH), 1.37 (9H, s, 3×$CH_3$).

13C-NMR ($CDCl_3$, 50 MHz, δ vs $SiMe_4$): 195.67 (C=O), 155.70, 149.98, 149.00, 147.84, 145.74, 141.81, 140.42, 137.13, 135.03, (all quaternary carbons); 130.66, 130.01, 129.86, 128.95, 127.86, 127.82, 125.58, 125.00, 124.18, 123.86, 120.76, 120.10, 119.32 (all CH); 65.95 (C-spiro); 34.09 (C(Me)$_3$), 31.08 (CH$_3$); ESI-MS (negative mode): 475.9 (M−H$^+$).

IR (CCl$_4$, cm$^{-1}$): 1660 (C=O).

2,2'-di-(4-tert-butyl)-benzoyl-9,9'-spirobifluorene (mixture of VIIIa and VIIIb) (C47H40O2):

1H-NMR (CDCl$_3$, 200 MHz, δ vs SiMe$_4$): 8.00-6.75 (22H, m, ArH), 1.34 (18 H, s, 6×CH$_3$).

13C-NMR (CDCl$_3$, 50 MHz, δ vs SiMe$_4$): 195.60 (C=O), 155.81, 149.01, 148.22, 145.89, 140.51, 137.13, 135.01 (all quaternary carbons); 130.95, 129.85, 129.06, 128.11, 125.38, 125.04, 124.10, 121.00, 119.49 (all CH); 65.72 (C-spiro), 34.09 (C(Me)$_3$), 31.03 (CH$_3$).

ESI-MS (negative mode): 655.6 (M+H$_2$O);

IR (CCl$_4$, cm$^{-1}$): 1660 (C=O).

Example 14

Preparation of a Mixture of Xa and Xb: Alternative Method a) Preparation of 2,2'-diacetyl-9,9'-spirobifluorene 2.95 g of finely divided anhydrous AlCl$_3$ (22.12 mmol) are added to 1.0 g of 9,9'-spirobifluorene (3.16 mmol) dissolved in 20 ml of carbon sulphide. 0.5 g of CH$_3$COCl (6.32 mmol) are added to 20 ml of carbon sulphide drop wise under stirring for 10'. The mixture is then refluxed during one hour and dried in a Rotavapor. It is decomposed with 50 g of ice and 25 ml of HCl 2N and the organic phase is extracted with dichloromethane; the organic extracts are recombined, washed with water and dried on anhydrous sodium sulphate.

Purification is performed by means of liquid chromatography, using a CH$_2$Cl$_2$ hexane 40:60 mixture as eluant to give 1.01 g of 2,2'-diacetyl-9,9'-spirobifluorene (C29H20O2; MW=400.48; yield 80%) (m.p.=255-257° C.).

b) Preparation of the 2,2'-dicarboxylic acid of the spirobifluorene.

0.6 ml of bromine (11.68 mmol) and then 0.75 g of 2,2'-diacetyl-9,9'-spirobifluorene prepared as above (1.88 mmol) and a few drops of THF (tetrahydrofuran) are added drop wise under stirring to a solution of NaOH (1.5 g in 20 ml of water) at 0° C. After refluxing, the solution is stirred for 4 hours; the pale yellow solution is then treated with a saturated solution of Na$_2$S$_2$O$_3$ until the colour disappears. After acidification with diluted HCl (3 N), the THF is eliminated via the Rotavapor and the water phase is extracted with CH$_2$Cl$_2$ several times; the combined extracts are washed in water and left to dry on anhydrous sodium sulphate. After column purification (eluant AcOEt:CHCl$_3$=10%), 420 mg of the 2,2'-dicarboxylic acid of the spirobifluorene (C27H16O4; MW=404.43; yield 55%) are obtained in the form of clear prisms like water, m.p. 352° C.

1H-NMR (CDCl$_3$, 200 MHz, δ vs SiMe$_4$) 6.61-7.81 (14H, m, Ar—H)

13C-NMR (CDCl$_3$, 50 MHz, δ vs SiMe$_4$): 206.63 (C=O); 167.09, 149.78, 149.17, 147.24, 141.58 (all quaternary carbons); 130.91, 130.17, 129.35, 125.61, 124.75, 122.30, 121.30 (all CH); 66.52 (C-spiro)

c) Preparation of the 9,9'-spirobifluorene 2,2'-dicarbonyl dichloride 3 drops of DMF are added to a solution containing 2 g of SBF(COOH)$_2$ prepared as above (5 mmol) in 20 ml of SOCl$_2$ (275 mmol) and the mixture is refluxed for 4 hours. After cooling, the excess thionyl chloride is removed under reduced pressure; petroleum ether (30-50° C.) is added and distillation is performed in a vacuum to obtain the raw acid chloride SBF(COCl)$_2$ (C27H14Cl2O2; MW=441.32; yield: ca 60%).

d) Preparation of the 2,2'-di-(4-tert-butyl)-benzoyl-9,9'-spirobifluorene 0.66 g of finely powdered anhydrous AlCl$_3$ (MW=133.3, 4.98 mmol) at 15° C. (water-ice bath) are added to 1 g of SBF(COCl)$_2$ prepared as above (MW=441.32; 2.27 mmol) in 20 ml of dichloromethane. 0.77 ml of tert-butylbenzene (MW=316.4, 4.98 mmol) are added drop wise under stirring for half an hour and the mixture is left to reach RT. It is then refluxed and stirring is continued for a further two hours. The mixture is decomposed with water and ice, then treated with diluted HCl and the organic phase extracted with dichloromethane.

The organic extracts are re-combined, treated with sodium carbonate, washed with water and dried on anhydrous sodium sulphate. This is followed by column chromatography using a mixture of 40% dicloromethane-hexane as eluant, to obtain the 2,2'-di-(4-tert-butyl)-benzoyl-9,9'-spirobifluorene.

TABLE 1

Standard potential for mono derivatives

| Products | E° (V vs SCE) |
|---|---|
| 2-(4-nitrobenzoyl)-9,9'-spirobifluorene | −0.81 |
| 2-(pentafluoro)-benzoyl-9,9'-spirobifluorene | −1.36 |
| 2-(2-furoyl)-9,9'-spirobifluorene | −1.49 |
| 2-(4-fluorobenzoyl)-9,9'-spirobifluorene | −1.60 |
| 2-benzoyl-9,9'-spirobifluorene | −1.62 |
| 2-(4-methoxybenzoyl)-9,9'-spirobifluorene | −1.64 |
| 2-(4-tert-buthylbenzoyl)-9,9'-spirobifluorene | −1.69 |

TABLE 2

Standard potential for di-derivatives

| Products | E° (V vs SCE) |
|---|---|
| 2,2'-di-(pentafluoro)-benzoyl-9,9'-spirobifluorene | −1.39 |
| 2,2'-di-(2-thienoyl)-9,9'-spirobifluorene | −1.47 |
| 2,2'-di-(4-fluorobenzoyl)-9,9'-spirobifluorene | −1.57 |
| 2,2'-di-(4-tert-buthylbenzoyl)-9,9'-spirobifluorene | −1.63 |
| 2,2'-dibenzoyl-9,9'-spirobifluorene | −1.65 |

In the above tables 1 and 2 there are shown the values of E° corresponding to the compounds prepared, calculated vs. SCE according to the following procedure. The apparatus used for the determination of the standard potentials of the described compounds was the AMEL System 5000.

The electrochemical technique used for the determination of the standard potentials of the described compounds was Cyclic Voltammetry.

The solvent system was tetraethylammonium perchlorate in acetonitrile 0.1 M; the cathode was a glassy carbon electrode; the anode was a platinum wire; the reference electrode was a saturated calomel electrode; the concentration of the substrate was 0.001 M; the sweep rate was 0.2 V/s.

The standard potentials (E°) of the described compounds were obtained from the formula: $E°=(E_{pc}+E_{pa})/2$ were $E_{pc}$ and $E_{pa}$ represent respectively, the cathodic peak potential and the anodic peak potential for the first reversible reduction process.

The standard potentials (E°) indicated for 2,2'-di-(4-fluorobenzoyl)9,9'-spirobifluorene and 2,2'-di-(pentafluoro)-benzoyl-9,9'-spirobifluorene were obtained subtracting 30 mV to the corresponding $E_{pc}$ values once extrapolated at sweep rate=0 V/s Example 15

General Procedure for the Synthesis of Radical Anions

The aprotic solvent, typically N,N-dimethylformamide, acetonitrile, or tetrahydrofuran, is dried according to usual procedures. An amount of supporting electrolyte, typically tetraethylammonium perchlorate, tetrabutylammonium tetrafluoroborate or lithium perchlorate, is dried according to usual procedures and added to the solvent in order to give a 0.1 M solution.

The chosen compound is added to the electrolytic solution in the cathodic section of a divided cell, under nitrogen flux, to give a concentration between 0.1 M and 0.1 mM, preferable between 0.01 M and 0.5 mM and particularly preferable 1 mM. In the cathodic section of the cell are placed a reticulated vitreous carbon (RVC) electrode as the cathode and a calomel electrode as the reference electrode. In the anodic section of the cell, divided from the cathodic section by a gelled electrolytic solution, a platinum gauze electrode, as the anode, is placed. A d.d.p. 0.2 V more negative than the standard potential E° (vs SCE) is applied.

Example 16

Synthesis of the Radical Anion of the Compound (Mixture of Xa and Xb)

Alumina (Riedel De Haen) pre-treated to 600° C. for 12 h to make it anhydrous is added to a portion of N,N-dimethylformamide (DMF) (Riedel De Haen). The DMF is then distilled twice under reduced pressure at a temperature not exceeding 27° C. A quantity of tetraethylammonium perchlorate $Et_4NClO_4$ (Fluka), previously dried at room temperature under vacuum for 24 h, is added to DMF so as to form a solution with concentration 0.1 M. The 9,9'-spirobifluorene-2,2'-di-(4-tert-butyl)-benzoyl (mixture of VIa and VIb) is added under nitrogen flux to the electrolytic solution in the cathodic compartment of a divided electrolytic cell in order to obtain a concentration 0.001 M. A cross-linked vitreous carbon electrode and the saturated calomel reference electrode (SCE) are placed in the cathodic compartment of the cell divided into two compartments. In the anodic compartment, separated from the cathodic compartment by the appropriately gelled electrolytic solution, a solution of 20 ml of N,N-dimethylformamide (DMF) (Riedel De Haen) containing 5 g of tetraethylammonium perchlorate $Et_4NClO_4$ (Fluka) is brought to boiling point, then 1 g of methylcellulose (BDH Chemicals) is added very slowly; boiling is maintained for approximately 5 minutes with stirring, then, while hot, the gelled solution is poured into the anodic compartment containing the Pt network anode. A d.d.p. of −1.6 V (vs. SCE) is applied between the electrodes.

The invention claimed is:

1. A spirobifluorene derivative which has the general formula (IV) and corresponding radical anions:

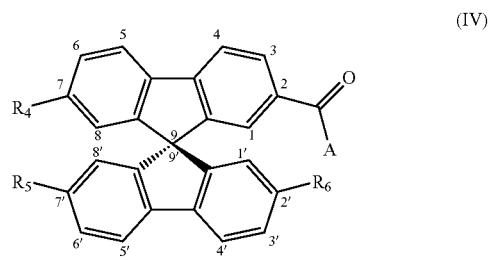

wherein $R_5$=A-C=O, and $R_4=R_6$=H; or $R_5$=A-C=O and $R_4=R_6=C_{1-4}$(alkyl); or $R_6$=A-C=O and $R_4=R_5$=H; or $R_6$=A-C=O and $R_4=R_5=C_{1-4}$(alkyl)

A is phenyl, biphenyl, 1-naphthyl, 2-naphthyl, 2-thienyl, 2-furyl, 2-pyrrolyl, 3-thienyl, 3-furyl, 3-pyrrolyl, 9-anthryl, perylenyl, fullerenyl, or a substituted derivative thereof.

2. A spirobifluorene derivative which has the following general formula (II) and corresponding radical anions:

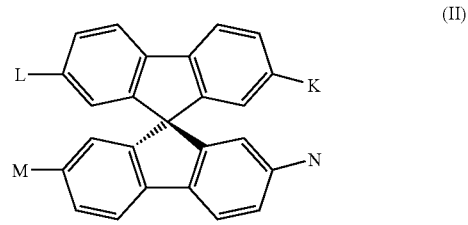

wherein L=M=H, K and N are A-C=O, with A=phenyl.

3. A spirobifluorene derivative which has the following general formula II and corresponding radical anions:

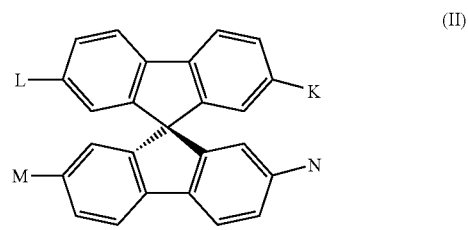

wherein L=N=H, K and M are A-C=O, with A=phenyl.

4. A spirobifluorene derivative which has the following general formula (II) and corresponding anionic radicals:

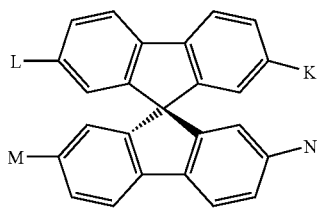

(II)

wherein L=N=H, K and M are A-C=O, with A=phenyl bearing at least one radical R and R=p-tert-Bu.

5. A spirobifluorene derivative which has the following general formula (II) and corresponding radical anions:

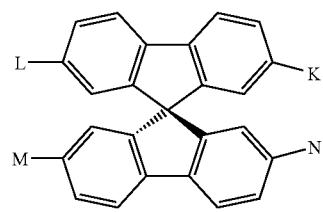

(II)

wherein L=M=H, K and N are A=O, with A=phenyl bearing at least one radical R and R=p-tert-Bu.

* * * * *